US009504827B2

(12) United States Patent
DeGiorgio et al.

(10) Patent No.: US 9,504,827 B2
(45) Date of Patent: *Nov. 29, 2016

(54) SYSTEMS, DEVICES AND METHODS FOR THE TREATMENT OF NEUROLOGICAL DISORDERS AND CONDITIONS

(71) Applicant: THE REGENTS OF THE UNIVERSITY OF CALIFORNIA, Oakland, CA (US)

(72) Inventors: Christopher M. DeGiorgio, Valencia, CA (US); Patrick Miller, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/721,300

(22) Filed: May 26, 2015

(65) Prior Publication Data

US 2016/0106979 A1    Apr. 21, 2016

Related U.S. Application Data

(63) Continuation of application No. 14/196,990, filed on Mar. 4, 2014, now abandoned, which is a continuation of application No. 12/898,675, filed on Oct. 5, 2010, now Pat. No. 8,688,220.

(Continued)

(51) Int. Cl.
*A61N 1/00* (2006.01)
*A61N 1/36* (2006.01)
*A61N 1/04* (2006.01)
*A61N 1/05* (2006.01)

(52) U.S. Cl.
CPC ......... *A61N 1/36025* (2013.01); *A61N 1/0456* (2013.01); *A61N 1/0476* (2013.01); *A61N1/0492* (2013.01); *A61N 1/0529* (2013.01); *A61N 1/0551* (2013.01); *A61N 1/3616* (2013.01); *A61N 1/36096* (2013.01); *A61N 1/36157* (2013.01); *A61N 1/36171* (2013.01); *A61N 1/36175* (2013.01)

(58) Field of Classification Search
CPC ............ A61N 1/0456; A61N 1/0476; A61N 1/0492; A61N 1/0529; A61N 1/36025; A61N 1/36; A61N 1/0551; A61N 1/36096; A61N 1/36157; A61N 1/3616; A61N 1/36171; A61N 1/36175

See application file for complete search history.

(56) References Cited

U.S. PATENT DOCUMENTS 3,279,468 A    10/1966  Le Vine
4,233,986 A    11/1980  Tannenbaum (Continued)

FOREIGN PATENT DOCUMENTS

JP    7289649 A    11/1995
JP    2007061267 A    3/2007

(Continued)

OTHER PUBLICATIONS

DeGiorgio, C. et al., Pilot Study of Trigeminal Nerve Stimulation (TNS) for Epilepsy: a Proof-of-Concept Trial, Epilepsia, 47(7): 1213-1215(2006).

Ahmed, H.E. et al., Use of Percutaneous Electrical Nerve Stimulation (PENS) in the Short-term Management of Headache, Headache, 40:311-315 (2000).

(Continued)

*Primary Examiner* — George Manuel
(74) *Attorney, Agent, or Firm* — Vista IP Law Group LLP (57) ABSTRACT

The present disclosure relates to methods, devices, and systems used for the treatment of and/or promoting recovery from various neurological disorders and conditions, including epilepsy and other seizure disorders and movement and other related disorders; for promoting recovery from acute or chronic brain injury (e.g. stroke, hypoxia/ischemia, head trauma, subarachnoid hemorrhage, and other forms of brain injury, for awakening and/or promoting the recovery of patients in various levels of coma, altered mental status or vegetative state); or for promoting recovery from chronic daily headache and migraine and related disorders via external (cutaneous) stimulation of the sensory branches of the trigeminal nerve in the face and forehead. More specifically, devices and electrode assemblies configured for stimulation of the supraorbital, supratrochlear, infraorbital, auriculotemporal, zygomaticotemporal, zygomaticoorbital, zygomaticofacial, nasal and infratrochlear nerves are disclosed.

2 Claims, 8 Drawing Sheets

Related U.S. Application Data (60) Provisional application No. 61/248,827, filed on Oct. 5, 2009, provisional application No. 61/289,829, filed on Dec. 23, 2009, provisional application No. 61/305,514, filed on Feb. 17, 2010, provisional application No. 61/354,641, filed on Jun. 14, 2010.

(56) References Cited

U.S. PATENT DOCUMENTS

| | | |
|---|---|---|
| 4,635,641 A * | 1/1987 | Hoffman ............... 600/391 |
| 5,514,175 A | 5/1996 | Kim et al. |
| 5,540,734 A | 7/1996 | Zabara |
| 5,814,095 A | 9/1998 | Muller et al. |
| 6,405,079 B1 | 6/2002 | Ansarinia |
| 6,549,808 B1 | 4/2003 | Gisel et al. |
| 6,567,702 B1 | 5/2003 | Nekhendzy et al. |
| 6,735,475 B1 | 5/2004 | Whitehurst et al. |
| 6,950,707 B2 | 9/2005 | Whitehurst |
| 6,954,668 B1 | 10/2005 | Cuozzo |
| 7,003,352 B1 | 2/2006 | Whitehurst |
| 7,171,276 B2 | 1/2007 | Giuntoli et al. |
| 7,502,652 B2 | 3/2009 | Gaunt et al. |
| 7,734,340 B2 | 6/2010 | De Ridder |
| 7,769,461 B2 | 8/2010 | Whitehurst et al. |
| 7,801,601 B2 | 9/2010 | Maschino et al. |
| 8,315,704 B2 | 11/2012 | Jaax et al. |
| 8,380,315 B2 | 2/2013 | Degiorgio et al. |
| 8,428,734 B2 | 4/2013 | Rigaux et al. |
| 8,494,641 B2 | 7/2013 | Boling et al. |
| 8,512,715 B2 | 8/2013 | Papay |
| 8,554,324 B2 | 10/2013 | Brocke |
| 8,565,896 B2 | 10/2013 | Ben-David et al. |
| 8,591,419 B2 | 11/2013 | Tyler |
| 8,666,498 B2 | 3/2014 | Newman |
| 8,688,220 B2 | 4/2014 | DeGiorgio et al. |
| 8,700,164 B2 | 4/2014 | DeGiorgio et al. |
| 8,958,880 B2 | 2/2015 | DeGiorgio et al. |
| 9,238,139 B2 | 1/2016 | DeGiorgio et al. |
| 2002/0077670 A1 | 6/2002 | Archer et al. |
| 2003/0195588 A1 | 10/2003 | Fischell et al. |
| 2004/0127965 A1 | 7/2004 | Borkan |
| 2004/0138097 A1 | 7/2004 | Guyuron |
| 2004/0172089 A1 | 9/2004 | Whitehurst et al. |
| 2004/0176820 A1 | 9/2004 | Paul, Jr. |
| 2004/0243207 A1 | 12/2004 | Olson et al. |
| 2005/0222657 A1 | 10/2005 | Wahlstrand et al. |
| 2005/0283198 A1 | 12/2005 | Haubrich et al. |
| 2006/0015153 A1 | 1/2006 | Gliner et al. |
| 2006/0050912 A1 | 3/2006 | Kidd et al. |
| 2006/0064140 A1 | 3/2006 | Whitehurst et al. |
| 2006/0167500 A1 | 7/2006 | Towe et al. |
| 2006/0173510 A1 | 8/2006 | Besio et al. |
| 2006/0200208 A1 | 9/2006 | Terry et al. |
| 2006/0206165 A1 | 9/2006 | Jaax et al. |
| 2006/0293723 A1 | 12/2006 | Whitehurst et al. |
| 2007/0049988 A1 | 3/2007 | Carbunaru et al. |
| 2007/0060975 A1 | 3/2007 | Mannheimer et al. |
| 2007/0150025 A1 | 6/2007 | Dilorenzo et al. |
| 2007/0150027 A1 | 6/2007 | Rogers |
| 2007/0173908 A1 | 7/2007 | Begnaud |
| 2007/0179557 A1 | 8/2007 | Maschino et al. |
| 2007/0233194 A1 | 10/2007 | Craig |
| 2007/0276451 A1 | 11/2007 | Rigaux |
| 2008/0046013 A1 | 2/2008 | Lozano |
| 2008/0103547 A1 | 5/2008 | Okun et al. |
| 2008/0128215 A1 | 6/2008 | Nowitz |
| 2008/0132980 A1 | 6/2008 | Gerber |
| 2008/0140151 A1 | 6/2008 | Brodkey |
| 2008/0147141 A1 | 6/2008 | Testerman et al. |
| 2008/0161713 A1 | 7/2008 | Leyde et al. |
| 2008/0171929 A1 | 7/2008 | Katims |
| 2008/0172101 A1 | 7/2008 | Bolea et al. |
| 2008/0262566 A1 | 10/2008 | Jaax |
| 2008/0269716 A1 | 10/2008 | Bonde et al. |
| 2008/0275327 A1 | 11/2008 | Faarbaek et al. |
| 2009/0048642 A1 | 2/2009 | Goroszeniuk |
| 2009/0210028 A1 * | 8/2009 | Rigaux et al. ............... 607/46 |
| 2009/0287035 A1 | 11/2009 | Dietrich et al. |
| 2010/0030227 A1 | 2/2010 | Kast et al. |
| 2010/0198044 A1 | 8/2010 | Gehman et al. |
| 2010/0198282 A1 | 8/2010 | Rogers |
| 2010/0222847 A1 | 9/2010 | Goetz |
| 2010/0228105 A1 | 9/2010 | Policker et al. |
| 2010/0228113 A1 | 9/2010 | Solosko et al. |
| 2010/0262205 A1 | 10/2010 | De Ridder |
| 2011/0093033 A1 | 4/2011 | Nekhendzy |
| 2011/0112603 A1 | 5/2011 | DeGiorgio et al. |
| 2011/0184489 A1 | 7/2011 | Nicolelis et al. |
| 2011/0218589 A1 | 9/2011 | DeGiorgio et al. |
| 2011/0218590 A1 | 9/2011 | DeGiorgio et al. |
| 2011/0270361 A1 | 11/2011 | Borsody |
| 2011/0282129 A1 | 11/2011 | Rigaux |
| 2011/0282412 A1 | 11/2011 | Glukhovsky et al. |
| 2011/0288610 A1 | 11/2011 | Brocke |
| 2012/0203301 A1 | 8/2012 | Cameron et al. |
| 2012/0330380 A1 | 12/2012 | Corndorf |
| 2013/0158626 A1 | 6/2013 | DeGiorgio et al. |
| 2014/0039572 A1 | 2/2014 | Bradley |
| 2014/0046407 A1 | 2/2014 | Ben-Ezra et al. |
| 2014/0081353 A1 | 3/2014 | Cook et al. |
| 2014/0081369 A1 | 3/2014 | Sosa et al. |
| 2014/0135886 A1 | 5/2014 | Cook et al. |
| 2014/0142669 A1 | 5/2014 | Cook et al. |
| 2014/0188200 A1 | 7/2014 | DeGiorgio et al. |
| 2014/0206945 A1 | 7/2014 | Liao |
| 2015/0151128 A1 | 6/2015 | DeGiorgio et al. |
| 2016/0106979 A1 | 4/2016 | DeGiorgio |
| 2016/0129254 A1 | 5/2016 | DeGiorgio et al. |

FOREIGN PATENT DOCUMENTS

| | | |
|---|---|---|
| JP | 2008506464 A | 3/2008 |
| JP | 2008-516696 A | 5/2008 |
| JP | 2008516696 A | 5/2008 |
| JP | 2008-246040 A | 10/2008 |
| JP | 2009-531154 A | 9/2009 |
| JP | 4961558 B2 | 6/2012 |
| JP | 2003-339884 A | 12/2013 |
| RU | 2086227 C1 | 8/1997 |
| RU | 2185092 C1 | 7/2002 |
| SU | 1718976 A1 | 3/1992 |
| WO | 2006/044792 A3 | 4/2006 |
| WO | 2006/044793 A2 | 4/2006 |
| WO | 2006044792 A2 | 4/2006 |
| WO | 2006/051370 A1 | 5/2006 |
| WO | 2007/136726 | 11/2007 |
| WO | 2008/128215 A1 | 10/2008 |
| WO | 2009/158389 | 12/2009 |
| WO | 2010/057998 A1 | 5/2010 |
| WO | 2011/044173 | 4/2011 |
| WO | 2011/044176 | 4/2011 |
| WO | 2011/044178 | 4/2011 |
| WO | 2011/044179 | 4/2011 |
| WO | 2012/075192 A2 | 6/2012 |
| WO | 2012/082960 | 6/2012 |
| WO | 2012/082961 | 6/2012 |
| WO | 2013/104552 A1 | 7/2013 |
| WO | 2013/152316 A1 | 10/2013 |

OTHER PUBLICATIONS

Allais, G. et al., Non-pharmacological approaches to chronic headaches: transcutaenous electrical nerve stimulation, astertherapy and acupuncture in transformed migraine treatment, Neuro Sci, 24:S138-S142(2003).

DeGiorgio, C. et al., Trigeminal nerve stimulation for epilepsy, Neurology, 61:421-422(2003).

Moseley, B.D. And DeGiorgio, C., Refractory status epilepsy, Neurology, 61:421-422(2003).

* cited by examiner

| PULSE DURATION (Usec) | 150us | 200us | 250us |
|---|---|---|---|
| mA'S RECORDED (MAX TOLERATED SETTINGS) | 7.92 | 5.94 | 5.72 |
| ELECTRODE RADIUS(cm) (1.25" DIAMETER ROUND ELECTRODES) | 1.59cm | 1.59cm | 1.59cm |
| SURFACE AREA cm | 7.92cm$^2$ | 7.92cm$^2$ | 7.92cm$^2$ |
| CURRENT DENSITY mA/cm$^2$ | 1 | .75 | .72 |
| MAXIMUM SAFE CURRENT DENSITY AT STIMULATING ELECTRODE mA/cm$^2$ | 25 | 25 | 25 |
| CHARGE DENSITY (A)(pulse)/cm$^2$ =uC/cm$^2$ AT STIMULATING ELECTRODE | .15 | .15 | 0.18 |
| MAXIMUM SAFE CHARGE DENSITY (uC/cm$^2$) AT BRAIN | 10 | 10 | 10 |

FIG.6

SYSTEMS, DEVICES AND METHODS FOR THE TREATMENT OF NEUROLOGICAL DISORDERS AND CONDITIONS

CROSS REFERENCE TO RELATED APPLICATIONS

This application is a continuation of U.S. application Ser. No. 14/196,990, filed Mar. 4, 2014, which is a continuation of U.S. application Ser. No. 12/898,675, filed Oct. 5, 2010, now U.S. Pat. No. 8,688,220, which in turn claims the benefit of priority under 35 U.S.C. §119(e) to the following applications: U.S. application Ser. No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

This application is also related to the following copending applications: U.S. application Ser. No. 12/898,685, entitled "Extracranial Implantable Devices, Systems and Methods for Treatment of Neuropsychiatric Disorders," filed on Oct. 5, 2010; U.S. application Ser. No. 12/898,686, now U.S. Pat. No. 8,380,315, entitled "Devices, Systems and Methods for Treatment of Neuropsychiatric Disorders," filed on Oct. 10, 2010; U.S. application Ser. No. 13/769,074 entitled "Devices, Systems and Methods for Treatment of Neuropsychiatric Disorders", filed Feb. 15, 2013; U.S. application Ser. No. 12/898,696, entitled "Extracranial Implantable Devices, Systems and Methods for Treatment of Neurological Disorders," filed on Oct. 5, 2010, and each of the above applications is hereby incorporated by reference as though fully set forth herein.

TECHNICAL FIELD

The present disclosure generally relates to cutaneous neurostimulator systems, devices and methods of using the same and more particularly relates to cutaneous neurostimulator systems, devices and methods for treating or promoting recovery from neurological disorders or conditions, such as seizure disorders, movement disorders, headache, acute or chronic brain injury, altered mental status/coma, and other brain-related disorders and conditions, by stimulating the superficial sensory branches of cranial nerves.

BACKGROUND

Neurological disorders and conditions, such as seizure disorders that are characterized by epileptic seizures, acute or chronic brain injury, coma, chronic headache or migraine, movement and related disorders, may be treated with medications and, in certain cases, brain surgery. For example, currently available treatment methods for epilepsy and other seizure related disorders may include stimulation of the nervous system by vagus nerve stimulation (VNS), which has been approved by the U.S. Food and Drug Administration. In this method, stimulating electrodes are surgically implanted on the vagus nerve in the neck. In addition to complications related to anesthesia, potential for infection, cost, and other adverse events with VNS, many of the subjects who undergo VNS treatments do not achieve relief from their seizures, and there is no reliable predictor of good outcomes from the implanted VNS device.

Other approaches are the focus of on-going research. For example, implantable approaches, including deep brain stimulation (DBS) of the anterior thalamus and intracranial stimulation of the epileptic zone via a device which monitors brain activity and delivers stimuli to terminate an impending seizure discharge, are also being studied. However, these methods are invasive and may have increased costs and side effects. Further, a substantial percentage of patients do not recover from or get adequate relief for the neurological condition or disorder despite multiple trials of pharmaceutical or surgical treatment.

SUMMARY

One aspect of the subject matter of the present disclosure addresses the aforementioned needs by providing a method of treating neurological disorders and conditions and a system and device configured to stimulate superficial (cutaneous) aspects of the ophthalmic (supra-orbital), infra-orbital, and mentalis branch(es) of the trigeminal nerve, specifically by providing a method of treating neurological disorders and conditions using cutaneous stimulation of the trigeminal nerve (TNS). In yet another aspect of the present disclosure, a method of treating neurological disorders and conditions using the disclosed electrode assembly is provided.

According to one aspect of the present invention, a method for treating a neurological disorder or condition by trigeminal nerve stimulation is provided. The method may include attaching an electrode assembly to a patient. The electrode assembly may include a first pair of contacts configured for placement on a first region of the patient's face; a second pair of contacts configured for placement on a second region of the patient's face; and an insulating connection region connecting the first pair of contacts and the second pair of contacts, wherein the first pair of contacts and the second pair of contacts are configured to contact a portion of the patient's face overlying at least one branch of the trigeminal nerve. The method may further include applying electrical signals to the electrode assembly at specified operational parameters to treat a neurological disorder or condition. In some embodiments, the operation of applying electrical signals may include applying the signals at a frequency between approximately 20 and 300 Hertz, at a pulse duration between approximately 50 and 500 microseconds, at an output current density of not greater than approximately 25 mA/cm$^2$ and/or an output charge density of not greater than approximately 10 microCoulomb/cm$^2$ at the cerebral cortex. In some embodiments, the electrode assembly is attached to the patient so as to contact the skin surface over at least one of an ophthalmic or a supraorbital nerve. In some embodiments, the neurological disorder or condition is epilepsy and other seizure related disorders. In some embodiments, the neurological disorder or condition is acute or chronic brain injury. In some embodiments, the neurological disorder or condition is chronic daily headache and migraine and related disorders. In some embodiments, the neurological disorder is a movement disorder.

In another aspect of the present disclosure, an electrode assembly may be configured for cutaneous trigeminal nerve stimulation. In some embodiments, the electrode assembly may be a component of a system or a kit. According to one aspect of the present disclosure, a cutaneous electrode assembly for trigeminal nerve stimulation is provided. The cutaneous electrode assembly may include a first electrode having a first pair of contacts configured for placement on a first region of a patient's face; a second electrode having a second pair of contacts configured for placement on a second region of a patient's face; and an insulating connection region connecting the (electrodes) first pair of contacts and the second pair of contacts, wherein the first pair of contacts and the second pair of contacts are configured to contact a portion of the patient's face overlying the cutaneous distribution of at least one branch of the trigeminal nerve for treatment of a neurological disorder or condition. The at least one branch of the trigeminal nerve may be selected from the group consisting of: superficial ophthalmic branch, infraorbital branch, and mentalis branch. In some embodiments, the electrode assembly may further include a retainer element configured to secure the electrode assembly to a patient's forehead.

In another aspect of the present disclosure, a system for trigeminal nerve stimulation for treatment of a neurological disorder or condition is disclosed. In one embodiment, the system includes a neurostimulator and a cutaneous electrode assembly including: a first electrode having a first pair of contacts configured for placement on a first region of the patient's face; a second electrode having a second pair of contacts configured for placement on a second region of the patient's face; and an insulating connection region connecting the electrodes and the first pair of contacts and the second pair of contacts, wherein the first pair of contacts and the second pair of contacts are configured to contact a portion of the patient's face overlying at least one branch of the trigeminal nerve. The system may further include a cable and/or lead wires operably or electrically connecting the neurostimulator and the cutaneous electrode assembly. In one embodiment, the at least one branch of the trigeminal nerve is selected from the group consisting of: superficial ophthalmic branch, infraorbital branch, and mentalis branch. The system may further include a retainer element configured to secure the electrode assembly to a patient's forehead.

In another aspect, a system for trigeminal nerve stimulation for treatment of a neurological disorder or condition is disclosed. In one embodiment, the system includes: a pulse generator; and a cutaneous electrode assembly in electrical communication with the pulse generator. The electrode assembly may include: a first electrode comprising at least one contact configured for cutaneous placement at a first region of the patient's face, wherein the first electrode is configured to contact a portion of the patient's face overlying at least one branch of the trigeminal nerve, wherein the system is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the assembly further comprises a second electrode comprising at least one contact configured for cutaneous placement at a second region of the patient's face, wherein the second electrode is configured to contact a portion of the patient's face overlying at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the first electrode and the second electrode are configured to contact a portion of the patient's face overlying a same branch of the trigeminal nerve. In some embodiments, the first electrode and the second electrode are configured to contact a portion of the patient's face overlying a different branch of the trigeminal nerve. The system may further include a wire operably connecting the pulse generator and the cutaneous electrode assembly. The system may further include a regulating device configured to regulate the maximum charge balanced output current below approximately 30-50 mA. The neurological disorder or condition is selected from the group consisting of: epilepsy, seizure related disorders, acute brain injury, chronic brain injury, chronic daily headache, migraine, disorders related to migraine and headache and movement disorders. In some embodiments, the pulse generator is configured to apply electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$ at the cerebral cortex.

In another aspect, a cutaneous electrode assembly for trigeminal nerve stimulation for treatment of a neurological disorder or condition is disclosed. In one embodiment, the assembly includes: a first electrode comprising at least one contact configured for cutaneous placement at a first region of the patient's face, wherein the first electrode is configured to contact a portion of the patient's face overlying at least one branch of the trigeminal nerve, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the assembly may further include a second electrode comprising at least one contact configured for cutaneous placement at a second region of the patient's face, wherein the second electrode is configured to contact a portion of the patient's face overlying at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiments, the first electrode and the second electrode are configured to contact a portion of the patient's face overlying a same branch of the trigeminal nerve. In one embodiment, the first electrode and the second electrode are configured to contact a portion of the patient's face overlying a different branch of the trigeminal nerve. The neurological disorder or condition is selected from the group consisting of: epilepsy, seizure related disorders, acute brain injury, chronic brain injury, chronic daily headache, migraine, disorders related to migraine and headache and movement disorders.

In another aspect, a method for treating a neurological disorder or condition by trigeminal nerve stimulation is disclosed. In one embodiment, the method comprises: contacting a first region of a patient's face with a cutaneous electrode assembly, the cutaneous electrode assembly comprising: a first electrode comprising at least one contact configured for cutaneous placement at a first region of the patient's face, wherein the first electrode is configured to contact a portion of the patient's face overlying at least one branch of the trigeminal nerve, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve; and applying electrical signals to the electrode assembly at specified operational parameters to treat a neurological disorder or condition. In one embodiment, the assembly further comprises a second electrode comprising at least one contact configured for cutaneous placement at a second region of the patient's face, wherein the second electrode is configured to contact a portion of the patient's face overlying at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the step of applying electrical signals comprises applying electrical signals at a frequency between approximately 20 and 300 Hertz, at a current of 0.05 to 5 milliamperes (mA) and at a pulse duration of less than or equal to 500 microseconds. In one embodiment, the step of applying electrical signals comprises applying electrical signals at a frequency between approximately 20 and 300 Hertz, at a pulse duration between approximately 50 and 500 microseconds, at an output current density of not greater than approximately 25 $mA/cm^2$ and an output charge density of not greater than approximately 10 $microCoulomb/cm^2$ at the cerebral cortex. The neurological disorder or condition is selected from the group consisting of: epilepsy, seizure related disorders, acute brain injury, chronic brain injury, chronic daily headache, migraine, disorders related to migraine and headache and movement disorders.

In another aspect, a kit for trigeminal nerve stimulation for treatment of a neurological disorder or condition is disclosed. The kit may include the cutaneous electrode assembly as described herein and instructions for placement of the electrode assembly on a patient for treatment of a neurological disorder or condition. The kit may further include a neurostimulator and instructions for applying electrical signals to the electrode assembly for treatment of a neurological disorder or condition.

BRIEF DESCRIPTION OF THE DRAWINGS

The present disclosure, both as to its organization and manner of operation, may be understood by reference to the following description, taken in connection with the accompanying drawings, in which.

DETAILED DESCRIPTION

The present disclosure relates to methods, devices, and systems used for the treatment of and/or promoting recovery from various neurological disorders and conditions, including epilepsy and other seizure disorders and movement and other related disorders; for promoting recovery from acute or chronic brain injury (e.g. stroke, hypoxia/ischemia, head trauma, subarachnoid hemorrhage, and other forms of brain injury, for awakening and/or promoting the recovery of patients in various levels of coma, altered mental status or vegetative state); or for promoting recovery from chronic daily headache and migraine and related disorders via external (cutaneous) stimulation of the sensory branches of the trigeminal nerve in the face and forehead. More specifically, devices and electrode assemblies configured for stimulation of the sensory components of the ophthalmic nerve and its branches, the infraorbital nerve and its branches, and the mentalis nerves or its branches, and including the supraorbital, supratrochlear, infraorbital, auriculotemporal, zygomaticotemporal, zygomaticoorbital, zygomaticofacial, nasal and infratrochlear nerves. Methods for the treatment of seizure disorders, such as epilepsy, and other neurological disorders and conditions by eTNS (external trigeminal nerve stimulation) are also provided. The methods, systems and devices described herein may be noninvasive or minimally invasive.

The methods, devices and systems described herein may also enhance neurological function, alertness, attention, and cognitive function after various forms of brain injury, e.g., stroke, head injury, hypoxic/ischemic brain injury, and/or other forms of acute and chronic brain injury and/or with respect to movement and other related disorders. The use of a cutaneous device as described herein may allow for rapid intervention soon after brain injury thereby possibly enhancing neurological recovery by stimulating the cutaneous branches of the trigeminal nerve. The unique anatomy of the trigeminal nerve, and its direct and indirect projections to key areas of the brainstem, thalamus and cortex involved with sensory processing, attention, and autonomic function, may allow the use of external stimulation for a variety of neurological conditions in which stimulation may be desirable.

In some clinical situations, brain stimulation has been found to be of sufficient clinical use to have been approved by the US Food and Drug Administration, for example, electroconvulsive therapy (ECT) and repetitive transcranial magnetic stimulation (rTMS) for psychiatric conditions. Some brain stimulation methods aim to generate currents in large volumes of the cortex and treat the brain as a bulk conductor, for example, ECT at the whole-lobe level and rTMS at the large regional level (i.e. dorsolateral prefrontal cortex). Additionally, deep brain stimulation is generally predicated on stimulation of small but regional volumes that lead to discharges in a very large number of cells. The systems, devices and methods of the present disclosure send minimal, if any, current into the brain; instead, signals are sent into the brain in order to modulate the activity of relevant neuroanatomical structures. Without wishing to be bound by any particular theory, the electrical pulses generate signals in the cutaneous branches of the trigeminal nerve and the electric fields are generally confined to the skin tissue and there is minimal, if any, leakage into the brain. These electrical pulses trigger a cascade of change in neuronal signaling events that involve very limited and precise recruitment of specific networks of neurons. The neuroanatomic pathways allow targeted modulation of activity in areas involved in epilepsy and other neurological conditions and disorders (e.g. locus coeruleus, anterior cingulate, insular cortex). Thus, the systems, devices and methods as disclosed herein utilize the brain's existing infrastructure to transmit signals to the targets of interest. In the context of this disclosure minimal current penetration means (1) a charge density of approximately 0 uC/cm2 at the cerebral cortex, or (2) calculated, measured, or modeled charge densities below the following thresholds: (a) at currents, charge densities, or charge per phase not likely to cause activation of pyramidal neurons and axons; and (b) to prevent brain injury, a charge density of less than 10 µC/cm2 in one embodiment, and, in other embodiments, a charge density of less than 0.001 to 0.1 µC/cm2, and at combinations of charge density and charge per phase not known to cause brain injury. In some embodiments, a lower charge density may be used when the central nervous system of an individual patient is sufficiently sensitive to lower levels of stimulation that the lower level will still permit clinical benefit to accrue.

The following description is provided to enable any person skilled in the art to make and use the subject matter of this disclosure, and it sets forth the best modes contemplated by the inventors of carrying out the various aspects of the disclosure. Various modifications, however, will remain readily apparent to those skilled in the art, since the principles of the disclosed subject matter have been defined herein specifically to describe: (1) systems and electrode assemblies configured for cutaneous trigeminal nerve stimulation; and (2) methods of treating neurological disorders and conditions, including epilepsy and other seizure disorders, by superficial trigeminal nerve stimulation using the electrode assembly.

Figure 1A:
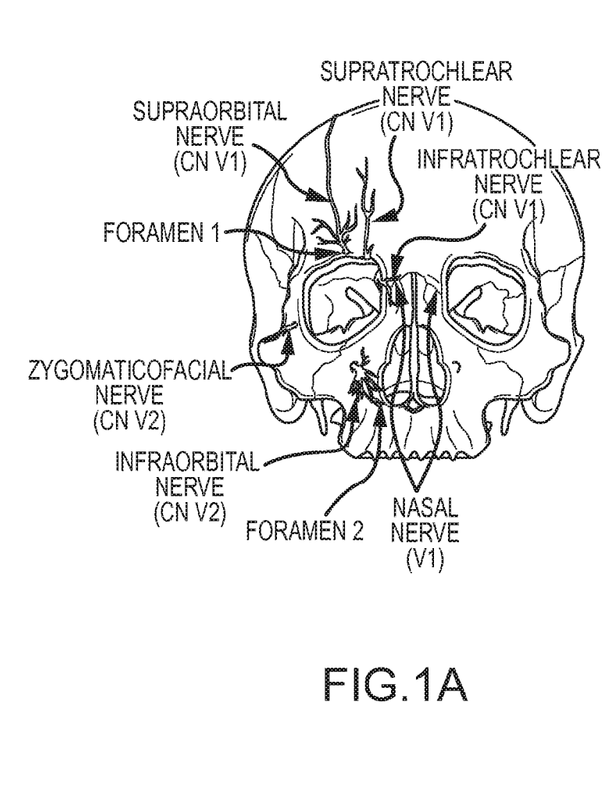
FIG. 1A-FIG. 1B illustrate the location of several branches (nerves) of the trigeminal nerve and the location of the major foramina for the superficial branches of the trigeminal nerve.
Figure 1B:
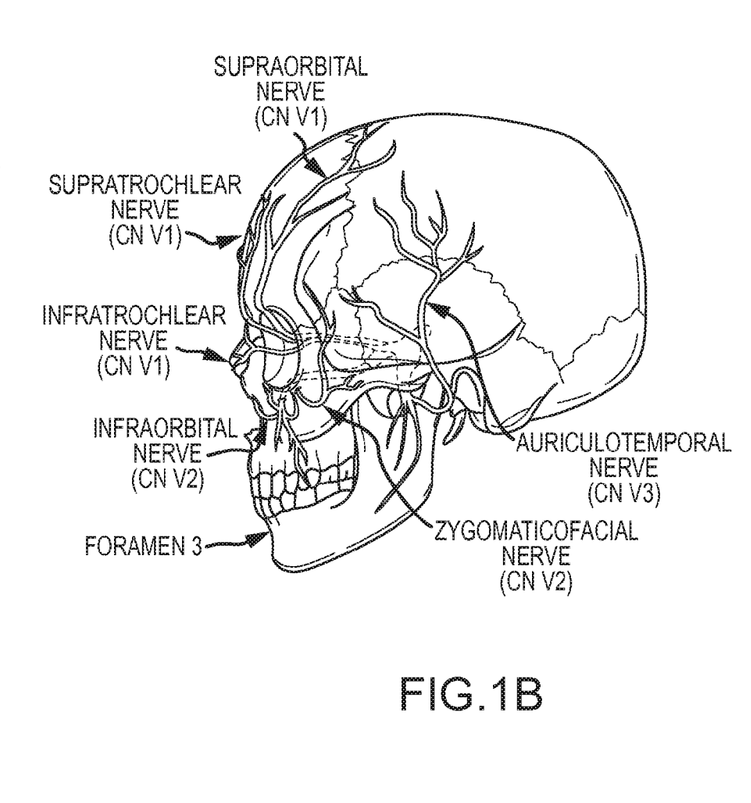

For a discussion related to the trigeminal nerve, reference is first made to FIGS. 1A-1B, which illustrate the location of several branches of the trigeminal nerve and the location of the major foramina for the superficial branches of the trigeminal nerve. The trigeminal nerve is the largest cranial nerve and has extensive connections with the brainstem and other brain structures. The trigeminal nerve has three major sensory branches over the face, all of which are bilateral, and highly accessible. The supraorbital nerve, or ophthalmic nerve, is frequently referred to as the V1 division. The infraorbital branch, or the maxillary nerve, is commonly referred to as the V2 division. The superficial branch, or the mandibular nerve (also known as the mentalis branch), is referred to as the V3 division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the jaw, tongue, and lower lip.

As can be understood from FIGS. 1A and 1B, these branches exit the skull through three foramina. The supraorbital nerve or ophthalmic nerve exits at foramen 1 (the supraorbital foramen or notch), approximately 2.1-2.6 cm from the nasal midline (in adults), and is located immediately above the orbital ridge that is located below the eyebrow. The nasal nerve is a division of the ophthalmic nerve. The infraorbital branch or maxillary nerve exits at foramen 2 (the infraorbital foramen), approximately 2.4-3.0 cm from the nasal midline (in adults) and the mentalis nerve exits at foramen 3 (the mentalis foramen) approximately 2.0-2.3 cm from the nasal midline (in adults). Other sensory branches, including the zygomaticofacial, zygomaticoorbital, zygomaticotemporal, and auriculotemporal, arise from other foramina Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus and then project to the cerebral cortex. Light touch sensory fibers are large myelinated fibers, which ascend to the ventral posterior lateral (VPL) nucleus of the thalamus. Afferent sensory fibers project from the trigeminal nuclei to the thalamus and the cerebral cortex.

The trigeminal nucleus has projections to the nucleus tractus solitarius (NTS), the locus ceruleus, the cerebral cortex, and the vagus nerve. The NTS receives afferents from the vagus nerve and trigeminal nerve. NTS integrates input from multiple sources, and projects to structures in the brainstem and forebrain, including the locus ceruleus.

The locus ceruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus ceruleus is a core part of the brainstem noradrenergic pathway, and produces the neurotransmitter norepinephrine. Norepinephrine plays a key role in attention, alertness, blood pressure and heart rate regulation, anxiety and mood.

While not wishing to be bound by any particular theory, in certain embodiments, the connections between the trigeminal nerve, locus coeruleus, nucleus and tractus solitarius, thalamus, and cerebral cortex, may be relevant to a potential role of the trigeminal nerve in numerous neurological disorders, including coma and brain injury, seizure disorders, headache, migraine, and movement disorders, as may be apparent to one skilled in the art. Thus, cutaneous stimulation of the trigeminal nerve at custom tailored settings and parameters within a predefined range could be effective in the treatment of multiple neurological disorders.

Neurological Disorders

Coma and Vegetative State.

Subcutaneous neurostimulation may improve consciousness in persons in coma and vegetative state. Without wishing to be bound by a particular theory, the brainstem reticular activating system (including locus coeruleus) and thalamus may play a role in alerting, awakening, and activating higher cortical structures. Stimulation of these and other brain structures, to which the trigeminal nerve and nuclei project, could assist in promoting awakening in coma, as well as recovery of cognition and motor function after various forms of brain injury. Given the projections of the trigeminal nerve to key brainstem, thalamic, and cortical structures involved in wakefulness and consciousness, the trigeminal nerve represents one method to activate these key structures.

Headache and Migraine.

Without wishing to be bound by a particular theory, headache and migraine involve pathways linked to the trigeminal nerve. Activation of specific trigeminal structures and pathways may play a role in headache. (Nature Medicine 2002; 8:136-142). Afferent trigeminal nerve fibers from vascular structures in the pia covering the cerebral cortex are activated, and activate or sensitize the trigeminal ganglion and the caudal trigeminal nuclei, which in turn activate the superior salvitory nucleus and the sphenopalatine ganglia. (Nature Medicine 2002; 8:136-142). Projections from these structures to vessels in the dura mater (the outer protective lining of the brain) lead to the release of vasoactive peptides, protein extravasation, and activation of nitric acid pathways, all of which result in dilatation of dural vessels, which may lead to headache. This is frequently referred to as the trigeminal-vascular reflex, and may be a mechanism in the genesis of migraine. (Nature Medicine 2002; 8:136-142). Without wishing to be bound by a particular theory, surgically lesioning or blocking the trigeminal nerve may inhibit this response, leading to a reduction in the cascade of events involved with migraine and other headache syndromes. As disclosed herein, acute or chronic electrical stimulation of the trigeminal nerve via its cutaneous or superficial braches in the face, at frequencies which inhibit the circuit described above, is one method to modulate this trigeminal-vascular reflex response, and reduce or inhibit headaches or migraines in which the trigeminal nuclei and nerves play a role.

Movement Disorders.

Movement disorders are characterized by involuntary movements of the body, and include, but are not limited to, tremors, twitches, and spasms, involuntary increases in tone of muscles, such as dystonias, and complex movements, such as dyskinesias and choreas. Without wishing to be bound by any particular theory, we hypothesize that TNS may modulate activity in key structures involved in movement disorders, including but not limited to the thalamus, basal ganglia, brain stem, and cerebral cortex, and may inhibit, by afferent stimulation, abnormal neuronal activity in motor systems which give rise to these involuntary phenomena.

Tardive and Other Dyskinesias.

Many medications which act on the dopaminergic neurons in the brain have a liability for inducing involuntary movements. This has been reported for treatment of Parkinson's disease with levodopa, for the use of neuroleptic medications in psychosis, bipolar disorder, and other conditions (Damier, *Curr Opin Neurol* 22:394-399, 2009), and for dopaminergic medications used to address gastrointestinal symptoms (Rao and Camilleri, *Ailment Pharmacol Ther* 31:11-19. 2010). Other individuals may suffer from dyskinesia on a genetic-related basis (Coubes et al., *Lancet* 355:2220-1, 2000). These dyskinesia syndromes consist of involuntary movements that usually start orofacially, with the muscles of the tongue, lips, mouth or face, but can increase in severity and come to involve other parts of body. The exact mechanisms by which these dyskinesias arise is not clear, but surgical treatment approaches have implicated the thalamus and the globus pallidum as locations where deep brain stimulation can lead to improvement (Kupsch et al., *J Neurol* 250 Suppl 1:147-152 2003). While not wishing to be bound by any particular theory, the connections between the trigeminal nerve, nucleus and tractus solitarius, and thalamus may provide a mechanism by which trigeminal nerve stimulation can ameliorate symptoms of dyskinesia by activating these key structures.

Seizure Disorders.

Without wishing to be bound by any particular theory, trigeminal nerve stimulation may modulate activity in the locus coeruleus, brainstem, thalamus, and cerebral cortex, and may activate inhibitory mechanisms and pathways which affect neuronal excitability. Trigeminal nerve stimulation may also inhibit excitatory mechanisms and pathways, resulting in inhibition of epileptic discharges and their spread in cortex, and subcortical structures. These processes may have a direct or indirect effect on activity in the epileptic focus itself Accordingly, stimulation of the superficial or cutaneous branches of the trigeminal nerve as disclosed herein provides an avenue for non-invasive neuromodulation. Further, stimulation parameters can be tailored for the individual condition, such that the brainstem, thalamic, or cortical structures involved in the individual condition can be activated or inhibited depending on the pathophysiology of the condition being treated.

For a discussion of certain embodiments of methods, systems and devices using cutaneous electrodes according to aspects of the present disclosure, reference is made to FIGS. 2-4C. FIGS. 2-4C illustrate various embodiments of a cutaneous electrode assembly and system according to aspects of the present disclosure.

Figure 2:
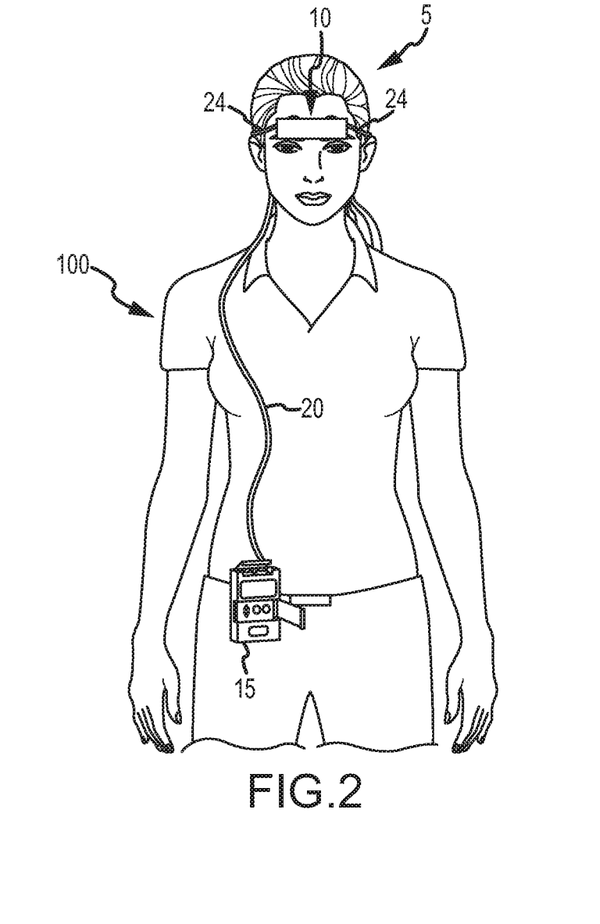
FIG. 2 shows an example of a subject wearing one embodiment of a cutaneous electrode assembly according to a method of neurological disorder and condition treatment by TNS provided according to aspects of the present disclosure.

One sample embodiment of the present disclosure takes the form of a method of treating epilepsy and related seizure disorders and other neurological disorders and conditions as described herein using trigeminal nerve stimulation ("TNS"). Broadly speaking, the method of treatment includes positioning external electrodes over or near at least one of the foramina or branches of the trigeminal nerve (FIG. 1A-1B), and stimulating the electrodes using a stimulator or pulse generator for a fixed time at specified operational parameters. In one embodiment, the external electrodes are positioned over the foramina of the supraorbital or ophthalmic nerves (FIG. 1A, Foramen 1) since unilateral or bilateral stimulation of the trigeminal nerve is achievable by placing single or separate electrodes on the right and/or left sides of a patient's face (e.g. by placing an electrode assembly, such as two separate electrodes, a single paired electrode or two pairs of electrodes, over the forehead or other region of the patient's face). In one embodiment, the electrode assembly is configured for unilateral stimulation. In one embodiment, the electrode assembly is stimulated for bilateral stimulation. In some embodiments, bilateral stimulation may offer similar or better efficacy than unilateral stimulation because the function of different brain structures may not be the same on right and left (e.g. verbal expression is most commonly localized to speech centers in the left hemisphere, and injury there produces catastrophic loss of the ability to speak, while damage to the corresponding region on the right does not produce this profound loss of function, but may alter subtle functions). There may also be synergistic effects that arise with bilateral stimulation. FIG. 2 shows an example of a patient 5 wearing an electrode assembly 10 on the forehead, corresponding to the foramina of the ophthalmic nerves. In alternative embodiments, the electrode assembly 10 can be positioned over the foramina of the maxillary nerves (FIG. 1A, Foramen 2) or the mandibular nerves (FIG. 1B, Foramen 3). In yet other embodiments, the stimulation can be unilaterally applied to one foramen of the trigeminal nerves. In other embodiments, the method of treating epilepsy and related seizure disorders and other neurological disorders and conditions as described herein comprises positioning external electrodes over a plurality of foramina and simultaneously stimulating different trigeminal nerves. In other embodiments, electrodes may be positioned at a region of the patient's face (on the right and/or left side) corresponding with the supratrochlear nerve, infratrochlear nerve, zygomaticotemporal, zygomaticofacial, zygomaticoorbital, nasal and/or auriculotemporal nerves and/or their respective foramina.

In one embodiment, as can be understood from FIGS. 2-4C, a system 100 for treatment of neurological disorders and conditions via TNS includes an electrode assembly 10, a neurostimulator or pulse generator 15 and electrical cable or wire 20. The electrode assembly 10 may be configured for the bilateral simultaneous and asynchronous stimulation of the ophthalmic nerves. In other embodiments, the electrode assembly may be configured for unilateral or bilateral stimulation of one or more branches of the trigeminal nerve as disclosed elsewhere herein. The neurostimulator or pulse generator may be any type of appropriate stimulating, signal-generating device. In the illustrated embodiment, the stimulator 15 is portable and attached to the belt of the patient 5. However, either a portable or non-portable stimulator can be used. In one embodiment, the electrical cable or wire 20 is configured to provide a physical and electrical link between the stimulator 15 and the electrode assembly 10 via lead wires. In other embodiments, the stimulator 15 and the electrode assembly 10 communicate wirelessly (i.e. the wire 20 and lead wires are not used). The system 100 and/or the electrode assembly 10 may be a part of a kit. In some embodiments, the kit may also include instructions for placement of the electrode assembly and/or the system. In some embodiments, the kit may also include instructions for treatment of a neurological disorder or condition according to a method disclosed herein.

Figure 3A:
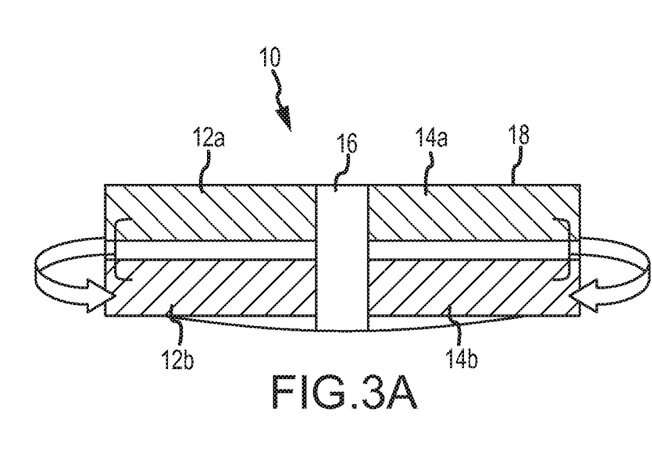
FIG. 3A is an enlarged view of the cutaneous electrode assembly of FIG. 2.
Figure 3B:
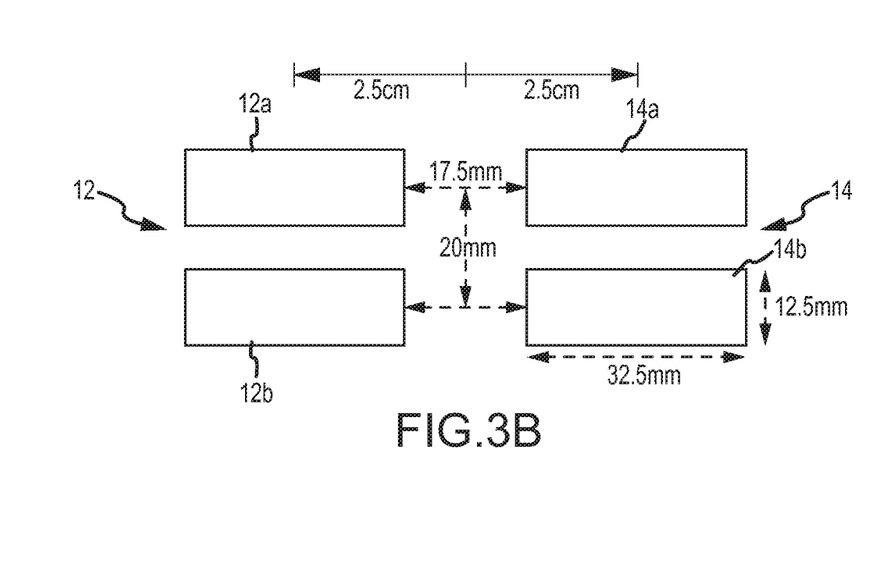
FIG. 3B illustrates representative dimensions of the cutaneous electrode assembly of FIG. 3A.

The cutaneous electrode assembly 10 shown in the illustrated embodiment is also referred to as a bilateral supraorbital electrode. As shown in FIGS. 3A and 3B, the electrode assembly 10 includes a first pair of electrodes (also referred to as contacts) 12a, 12b for placement on a first region of the patient's face, and a second pair of electrodes (also referred to as contacts) 14a, 14b for placement on a second region of the patient's face. In some embodiments, the first region is the right side of the patient's face and the second region is the left side of the patient's face. The first pair of contacts comprises a first upper contact 12a and a first lower contact 12b, while the second pair of contacts comprises a second upper contact 14a and a second lower contact 14b. An insulative connection region 16 connects the first and second contact pairs to each other. The electrode assembly 10 comprises an inner contact surface 18 that comes into contact with a patient's skin at four contact areas, each corresponding to one of the four contacts 12a, 12b, 14a, 14b. The inner contact surface 18 comprising the four contact areas may also include a buffered gel-like adhesive that provides good electrical conductivity with minimum skin irritation, an example of such gel includes the commercially available hydrogels from AmGel Technologies (AmGel Technologies, Fallbrook, Calif. USA).

Optionally, the electrode assembly 10 comprises a retainer element 24 configured to secure the electrode assembly to a patient's forehead. In one embodiment, the retainer element 24 can be an elastic band or strap. In alternative embodiments, the electrode assembly 10 can be secured in place by a hat, band, or a cap, which may also serve to conceal the electrode assembly from view or an appropriate adhesive.

In some embodiments, the system 100 may include a regulation device. The regulation device is configured to be attached to the pulse generator 15 and is configured to govern the maximum charge balanced output current below approximately 30-50 mA to minimize current penetration to the brain and increase patient tolerance. The regulation device may be internally programmed to range from 0.25-5.0 mA, 0-10 mA, 0-15 mA, depending on the surface area, placement, and orientation of the electrode, and whether the electrode is stimulating near or adjacent to the skull, or away from the skull, (mentalis), where current ranges may be higher or lower. Current TENS units stimulate with maximum output currents of up to 100 mA's, which result in currents which may penetrate the skull and which may not be well tolerated.

Figure 4A:
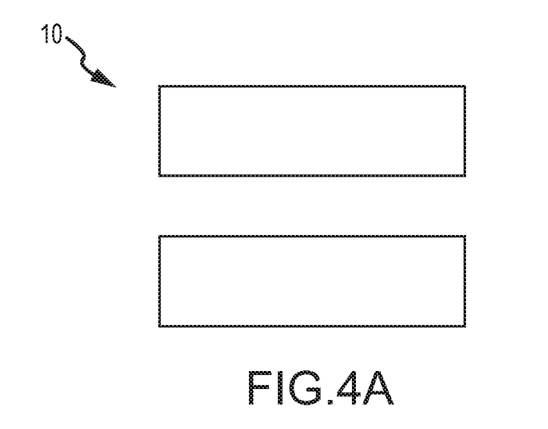
FIG. 4A-FIG. 4C depict various embodiments of the cutaneous electrode assembly of FIG. 2.
Figure 4B:
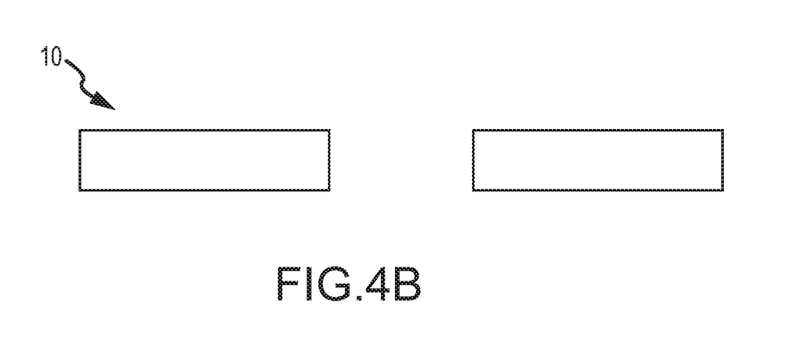
Figure 4C:
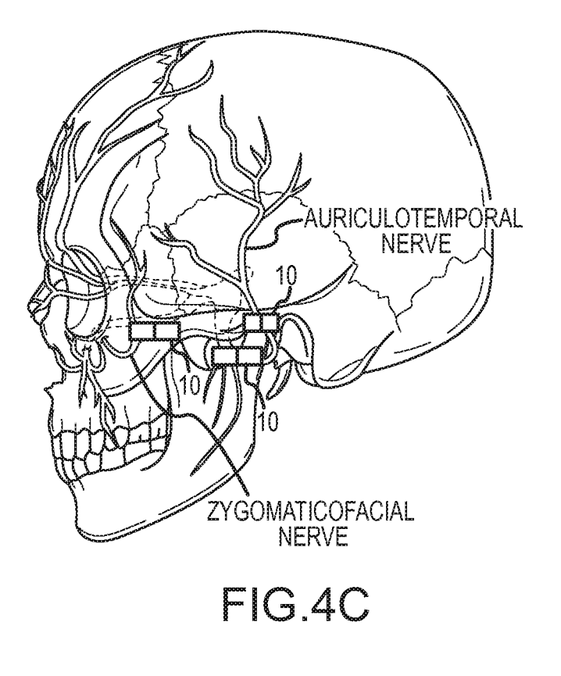

The electrode assembly 10 as shown in FIGS. 3A and 3B is configured to stimulate both the right and left ophthalmic nerves either simultaneously or asynchronously. The insulative connection region 16 serves to assist a patient in lining up the electrode assembly 10 with the midline of the nose to ensure proper placement of the electrode assembly 10 over both ophthalmic nerves, which lie on the average about 2.1 to 2.6 cm from the nasal midline of an adult patient. Thus, the electrode assembly can be placed accurately (e.g. by the patient) without knowledge of the location of the ophthalmic nerve or key landmarks relative to the nerve, thereby reducing the possibility of inadequate stimulation due to errors in positioning of the electrodes. FIGS. 4A-4C illustrate other embodiments of the electrode assembly 10, which configurations may be used to stimulate the right and/or left ophthalmic nerve and/or other branches of the trigeminal nerve as disclosed herein, such as the zygomaticofacial and/or the auriculotemporal nerves. It can be appreciated that a single electrode or multiple electrodes may be used. The bilateral supraorbital electrode is configured for bilateral supraorbital stimulation. It is scalable based on the location of use, stimulation parameters, and input from computer modeling so as to negate or minimize or render safe current penetration into the brain. As skin irritation may occur, a similar configuration could be applied unilaterally, so as to provide relief to one side of the forehead, to promote skin tolerability and to reduce the risk of irritation. Other configurations of size and inter electrode distance can be conceived for different branches of the trigeminal nerve, including but not limited to those as shown in FIGS. 4A-4C.

The placement of the first contact pair 12a, 12b and the second contact pair 14a, 14b on opposite sides of the nasal midline assures that stimulation current moves orthodromically or in the direction of the afferent ophthalmic or supraorbital nerve. Furthermore, this configuration of the electrode assembly 10 allows the contact pairs 12a,12b and 14a,14b to be stimulated independently and/or unilaterally, as the response to stimulus may be localized and thus varied from one side of the midline to the other side. That is, the presently disclosed electrode assembly permits individual adjustment of current for the first and second regions or right and left sides, as applicable, thereby reducing asymmetric stimulation and/or perceived asymmetric stimulation.

For stimulations wherein electrical pulses of a single polarity are generated, the upper contacts 12a, 14a and lower contacts 12b, 14b may have fixed polarities. For stimulations wherein electrical pulses of alternating polarities are generated, the upper contacts 12a, 14a and lower contacts 12b, 14b may have alternating polarities. Also, the inferior electrode typically serves as the cathode for the leading phase of the stimulating pulse. In the case of a monophasic stimulation, the inferior electrode generally becomes the cathode.

FIG. 3B illustrates the dimensions of one embodiment of the cutaneous or supraorbital electrode assembly of FIG. 2 to show the relative relationship of the electrodes from the midline and from each other. The size of the electrodes and the inter-electrode distance are sized to facilitate current delivery to the skin and nerve, while reducing and/or minimizing current density beyond the inner table ((dense layer) of the skull (inner skull bone). As explained in this disclosure, the systems, devices and methods of this disclosure are configured to minimize current penetration into the brain.

Dimensions of one embodiment of the electrode assembly are shown in FIG. 3B. The surface area, relationship between the electrode contacts and the midline, and the inter-electrode distances are each important factors to minimize the potential for skin or nerve injury, for ensuring adequate stimulation of each nerve, and to minimize current flow (penetration) through the skull and into the brain tissue. The current flow to the electrode, the on/off time, time of use and frequency of stimulation are also important to ensure adequate safety and efficacy. The electrode dimensions are scalable for use with different output currents and pulse duration.

As can be understood from FIG. 3B, each contact 12a, 12b, 14a, 14b is sized to deliver an electrical pulse over a large enough surface area to minimize any skin injury due to excess charge density, and to minimize current penetration beyond the inner surface of the skull bone. The distance between the first contact pair 12a, 12b and the second contact pair 14a, 14b is configured to stimulate the ophthalmic nerves while minimizing any current delivery to the surface of the brain. In one embodiment, the mid-point of each of the electrodes is approximately 2.5 cm (range 2.1-2.6 cm) from the nasal midline. The electrode size and the inter-electrode distance may vary for children and adults, and for males and females. In one embodiment, the electrode is approximately 32.5 mm in length by 12 5 mm in height and the inter-electrode distance between, for example, the upper pair of electrodes 12a, 14a is 17 5 mm and the inter-electrode distance between, for example, the upper electrode 12a and the lower electrode 12b is 20 mm In other embodiments, the length of the electrode may be greater than or less than 32.5 mm and greater than or less than 12.5 mm in height. In still other embodiments, the inter electrode distance can be in a range greater than 20 mm and/or less than 17.5 mm Those of skill in the art will recognize that one or more of the above distances can be used as a border of a range of distances.

Those skilled in the art will appreciate that various adaptations and modifications of the above-described embodiments of the electrode assembly 10 are within the scope and spirit of the present disclosure. For example, one embodiment of the present device comprises a unilateral electrode assembly configured for the unilateral stimulation of ophthalmic nerves. Also, the instant electrode assembly can also be configured for the stimulation of the maxillary nerves or the mandibular nerves or other nerves as disclosed herein. As yet another example, an electrode assembly configured for the simultaneous stimulation of a plurality of trigeminal nerve branches is also within the scope of the present disclosure.

In use, the electrode assembly 10 is positioned over the forehead of the patient 5 such that the insulative connection region 16 lines up with the midline of the nose of the patient 5. In some embodiments, the electrode assembly 10 is placed over the supraorbital foramina, located over the orbital ridge approximately 2.1-2.6 cm lateral to nasal midline. In one embodiment, the electrode assembly 10 is then connected to a pulse generator 15 via the electrical cable 20. In other embodiments, the electrode assembly is connected to the pulse generator 15 via a wireless connection. Stimulation according to patient specific operational parameters as determined according to the methods described herein is then applied.

According to one aspect of the present disclosure, a method of treatment of epilepsy and related seizure disorders and other neurological disorders and conditions using the electrode assembly 10, as described above, is described. In one embodiment, the method of treating these neurological disorders and conditions includes positioning the electrode assembly 10 to the forehead of a patient, connecting the electrode assembly 10 to a stimulator, and stimulating the electrode assembly 10 at defined values of the operational parameters as disclosed herein to minimize current penetration into the brain/below the skull bone. In some embodiments, the electrode assembly is connected to the stimulator via wire 20 and/or lead wires. In some embodiments, the electrode assembly is wirelessly connected to the stimulator.

In one embodiment, the bilateral supraorbital electrode 10 illustrated in FIGS. 2-3B is stimulated at a stimulus frequency between about 20 Hz and about 300 Hz, at a pulse duration between 50 microseconds (μsec) to 250 μsec, at an output current density of less than approximately 25 mA/cm$^2$ and at no or negligible charge densities at the cerebral cortex, or calculated or measured charge densities at the cerebral cortex of less than 10 μC/cm$^2$ to reduce the risk of brain injury, and less than 1.0 μC/cm$^2$, and even 0.001-0.01 μC/cm$^2$ in some embodiments, and at combinations of charge density and charge per phase not known to cause brain injury for at least one-half to one hour per day or may be provided for up to 24 hours per day. It is possible that even lower charge densities may be desirable. Those of skill in the art will recognize that one or more of the above parameters can be used as a border of a range of parameters.

According to one aspect of the present disclosure, the method of treating epilepsy and related seizure disorders and other neurological disorders and conditions by TNS comprises selecting optimal values for the operational parameters for the stimulation of each individual patient. In one embodiment, the neurostimulation is provided using an electrical stimulator at the following exemplary settings: frequency 20-150 Hz, current 5-15 mA, pulse duration of 50-250 microseconds, a duty cycle of 10% to 50%, for at least one hour per day. In another embodiment, the neurostimulation is provided using an electrical stimulator at the following exemplary settings: frequency 20-150 Hz, current 1-10 mA, pulse duration of 50-250 microseconds, a duty cycle of 10% to 50%, for at least one hour per day.

In various embodiments, the stimulation is delivered at a specific pulse width or range of pulse widths (or pulse duration). The stimulation can be set to deliver pulse widths in the range greater than and/or less than one or more of 50 μs, 60 μs, 70 μs, 80 μs, 90 μs, 100 μs, 125 μs, 150 μs, 175 μs, 200 μs, 225 μs, 250 μs, up to 500 μs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 μA and an upper limit of about 30 mA-35 mA, depending on the surface area of the electrodes, inter-electrode distance, the branch(es) stimulated, and the modeling data as described above. In various embodiments, the amplitude can be in a range greater than and/or less than one or more of 50 μA, 75 μA, 100 µA, 125 µA, 150 µA, 175 µA, 200 µA, 225 µA, 250 µA, 275 µA, 300 µA, 325 µA, 350 µA, 375 µA, 400 µA, 425 µA, 450 µA, 475 µA, 500 µA, 525 µA, 550 IµA, 575 µA, 600 µA, 625 µA, 650 µA, 675 µA, 700 µA, 725 µA, 850 µA, 875 µA, 900 µA, 925 µA, 950 µA, 975 µA, 1 mA, 2 mA, 3 mA, 4 mA, 5 mA, 6 mA, 7 mA, 8 mA, 9 mA, 10 mA, 11 mA, 12 mA, 13 mA, 14 mA, 15 mA, 16 mA, 17 mA, 18 mA, 19 mA and 20 mA. Those of skill in the art will recognize that one or more of the above amplitudes can be used as a border of a range of amplitudes.

In various embodiments, the stimulation can be delivered at one or more frequencies, or within a range of frequencies. The stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles. The stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognize that one or more of the above percentages can be used as a border of a range of duty cycles.

In other embodiments, different values of the operational parameters may be used. In one embodiment, the values of the operational parameters are selected such that a patient will experience a stimulation sensation, such as a mild tingling over the forehead and scalp without being in discomfort or in pain. The neurostimulation parameters are important factors in the treatment method. In one embodiment, the values of the operational parameters are selected to minimize skin irritation, burns, undesired effects on the brain and/or the ophthalmic nerves. In one embodiment, the method of selecting operational parameters comprises evaluating variables such as the configuration and size of the electrode, the pulse duration, the electrode current, the duty cycle and the stimulation frequency, each of which are important factors in ensuring that the total charge, the charge density, and charge per phase are well within accepted safety limits for the skin, nerve and brain. For example, to minimize skin irritation, it is not sufficient to merely consider the total current, but the current density needs to be defined. Additionally, it is important to select the electrical stimulation parameters, electrode design, and inter-electrode distance, such that the electrical stimulation zone includes the ophthalmic nerve (approximately 3-4 mm deep) or other desired nerve branch, while preventing or minimizing current penetration beneath the skull bone and into the brain.

The stimulation is carried out at the above-described values of the operational parameters. The values of the operational parameters are advantageously selected such that a patient will experience a stimulation sensation, such as mild tingling over the forehead and scalp, without causing the patient unbearable discomfort or pain and to minimize current penetration into the brain. These values may vary according to the treatment of interest.

In some embodiments, an external device may be used to identify the location of the branch or branches of the trigeminal nerve that will be targeted in an individual patient for stimulation by an implanted electrode assembly. The external device may be used for mapping and targeting the desired branch or branches of the trigeminal nerve and for identifying the individual stimulation parameters that are optimal for efficacy and safety. In one embodiment, the device may include a plurality of external (transcutaneous) TNS electrodes. The practitioner approximates the location of the target branch and affixes the electrodes to the patient's skin above the target location. Stimulation may be applied and the actual location or preferred (optimal) stimulation location of the target branch or branches may be determined Stimulation parameters may also be established. Once the location and/or stimulation parameters have been established via the external device, that data may be used to help guide the placement of the implanted electrodes for an individual patient and to establish the customized stimulation parameters for that patient.

In addition, the use of external electrodes for stimulation of the trigeminal nerve may identify individuals who are likely to derive therapeutic benefit from a minimally invasive system in addition to the optimal specific locations and parameters of stimulation based on person-to-person variability. Various neurodiagnostic, imaging, or cutaneous nerve mapping methods may be able to delineate differences in individual anatomy to optimize stimulation for efficacy and/or safety. Furthermore, the use of a minimally invasive system may allow screening and identification of those individuals who are likely to derive benefit from other implantable systems, such as deep brain stimulation. This can be conceptualized as linking the three approaches as stage I (external TNS of the trigeminal nerve), stage II (implanted TNS of the superficial trigeminal nerve), and stage III (deep brain stimulation), such that stage I can screen for stage II, and stage II for stage III. By monitoring a patient for evidence of useful therapeutic effect, such as by reduction in the severity of symptoms, the results of treatment at one stage may be used to judge the likely effect of treatment with a more invasive treatment from a higher stage.

A method of evaluating the use of trigeminal nerve stimulation for treatment of a neurological disorder in a patient is disclosed herein. The method may include applying a cutaneous system for stimulation of the trigeminal nerve to the patient and monitoring the patient for at least one of evidence of a useful therapeutic response or evidence of tolerability of TNS treatment, providing a subcutaneous electrode assembly or system, and implanting the subcutaneous electrode assembly or system in the patient for treatment of a neurological disorder.

A method of evaluating the use of deep brain stimulation for treatment of a neurological disorder in a patient is disclosed herein. The method may include applying a cutaneous system for stimulation of the trigeminal nerve to the patient and monitoring the patient for at least one of evidence of a useful therapeutic response or evidence of tolerability of TNS treatment thereby generating external measurement criteria, providing a subcutaneous electrode assembly or system, implanting the subcutaneous electrode assembly or system in the patient for treatment of a neurological disorder, monitoring the patient for at least one of a useful therapeutic response or tolerability of the implanted device, thereby generating extracranial measurement criteria, and analyzing the external measurement criteria and extracranial measurement criteria to determine whether the patient will benefit from deep brain stimulation.

The following examples are presented to set forth more clearly the subject matter of this disclosure without imposing any limits on the scope thereof and to illustrate the clinical benefits of trigeminal nerve stimulation for the treatment of neurological disorders and conditions. In the examples, patients with epilepsy were treated by TNS with external cutaneous electrodes.

Example 1

Figure 5:
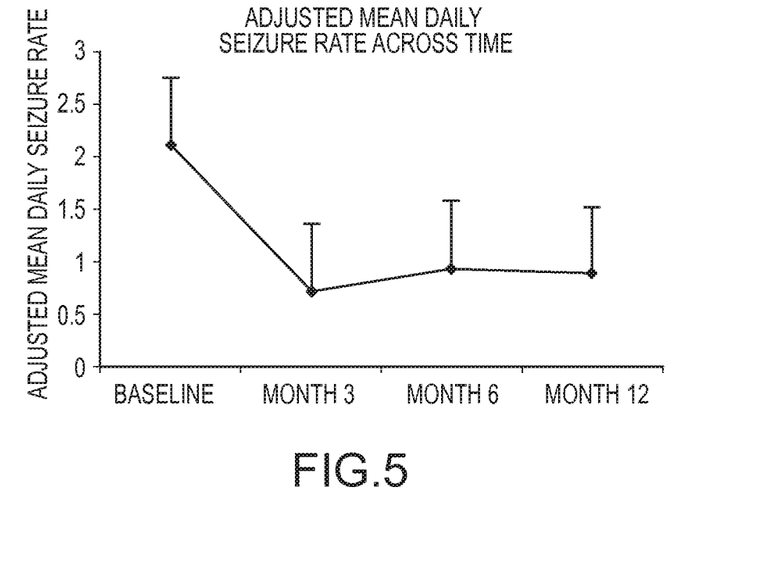
FIG. 5 illustrates the results from a pilot study of external trigeminal nerve stimulation ("TNS")

FIG. 5 illustrates the results from a pilot study of external trigeminal nerve stimulation. Subjects with epilepsy who met inclusion and exclusion criteria for a pilot feasibility study of external trigeminal nerve stimulation initially participated in a 1-month baseline period where seizures were counted, followed by active stimulation of the infraorbital or ophthalmic branch of the trigeminal nerve. Inclusion criteria were: subjects with poorly controlled epilepsy; ages 18-65 years; at least three complex-partial or generalized tonic-clonic seizures per month; no serious or progressive medical or psychiatric conditions; and exposure to at least 2 antiepileptic drugs (AED's). Subjects with a vagus nerve stimulator were excluded from the study. All subjects received unblinded TNS augmentation (adjunctive) treatment for at least 8-12 hours each day. Assessments were made at study intake and at monthly periodic visits for three months following the one month baseline. These initial assessments were then followed-up with visits to a neurologist skilled in epilepsy for three to six month intervals for up to three years or as approved by the local Institutional Research Committee.

Subjects underwent stimulation using an electrical stimulator, such as the EMS Model 7500 commercially available from TENS Products, Inc. at a frequency of 120 Hertz, a current less than 20 mA, pulse duration of 250 μsec, and a duty cycle at 30 seconds on and 30 seconds off, for a minimum of 8 hours.

FIG. 5 illustrates the results from this pilot study showing the effectiveness of external trigeminal nerve stimulation. Five of twelve subjects experienced greater than 50% reduction in adjusted mean daily seizure rate at 6 and 12 months of treatment. Mean reduction at 3 months was 66% and 59% at 12 months. (DeGiorgio et al, Neurology 2009; 72: 936-938). Overall, the data from the table of FIG. 5 show that the trigeminal nerve stimulation using the described operational parameter values was effective and well tolerated by the subjects tested. No serious adverse events were reported. Importantly, the therapeutic effect of the device was observed in several standard measures, indicating the broad-reaching benefits of this treatment on a variety of outcome measures.

Example 2

Figure 6:
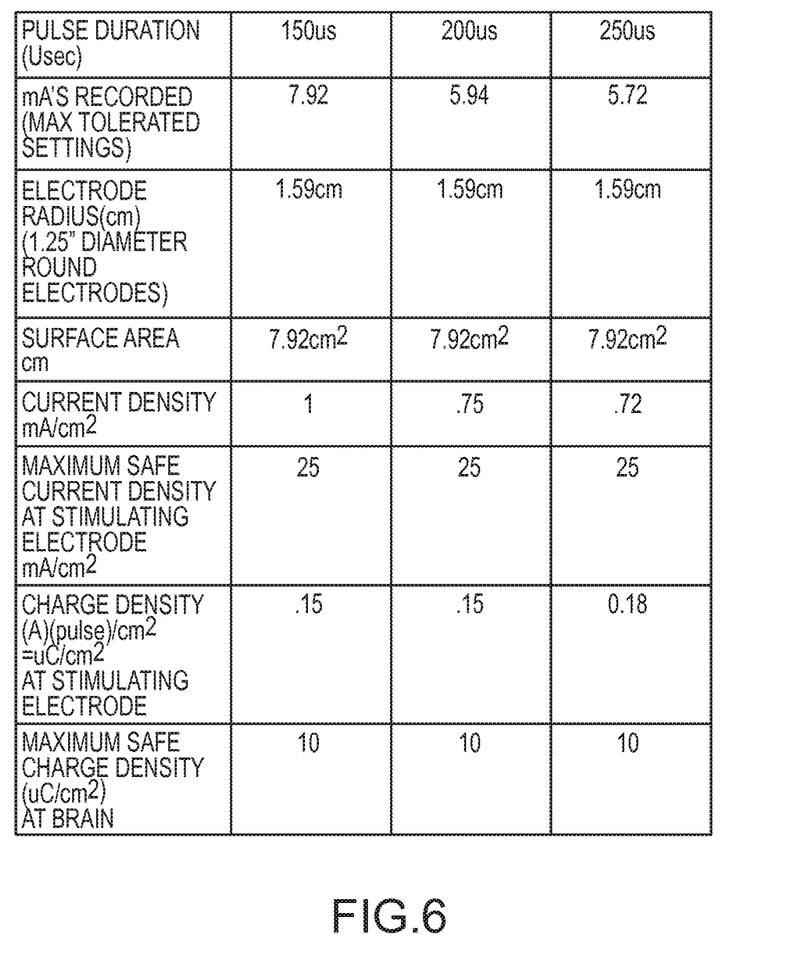
FIG. 6 summarizes one embodiment of current, charge, current density and charge density parameters for a subject exposed to cutaneous stimulation of the supraorbital nerve.

FIG. 6 summarizes current, charge, current density and charge density in a subject exposed to cutaneous stimulation of the supraorbital nerve. FIG. 6 illustrates representative parameters for bilateral supraorbital stimulation recorded in a subject using an EMS 7500 stimulator, 120 HZ, 150-250 μsec, Tyco superior silver electrodes 1.25", one inch from the midline above the eyebrows. Data recorded with Fluke Oscilloscope, 50 mV/div, resistor=10.1Ω. In general, these findings show that as the pulse width increased, the maximum tolerable current decreased.

Cutaneous electrical stimulation of the supraorbital branch of the trigeminal nerve with round 1.25-inch TENS patch electrodes results in current densities and charge density/phase that are well within the limits of safety. In general, the maximum current comfortably tolerated by TNS patients studied previously is approximately 25 mA, and patients typically are stimulated at an amplitude setting well below 25 mA (6-10 mA).

The 1.25-inch TENS electrodes are circular electrodes with a radius of 1.59 cm. The surface area can be calculated as $A=\pi r^2=[\pi]\times[1.59\ cm]^2=7.92\ cm^2$. Using these electrodes, typical stimulation current ranges from 6-10 mA at pulse durations of 150-250 μsec.

Current Density: In a typical subject, stimulation currents of 6-10 mA result in current densities ranging from 0.76 to 1.3 mA/cm². McCreery et al have established a maximum safe current density of 25 mA/cm² at the stimulating electrode for transcranial electrical stimulation. Assuming even higher currents of up to 25 mA with electrodes of surface area 7.92 cm², current densities may range to a maximum of 3.16 mA/cm². From 0.76 mA/cm² to 3.16 mA/cm², TNS delivers a current density 8-33 times less than the maximum safe allowable current density. Charge Density (Charge density/phase): Yuen et al have identified a safe limit for charge density/phase delivered at the cerebral cortex of 40 μC/cm² [Yuen et al 1981] and more recently McCreery et al. (McCreery et al 1990) have identified 10 μA C/cm² as the safe limit. Assuming 10 mA at 250 μsec, the charge density/phase is [0.010 A]×[250 μsec]/7.92=0.32 μC/cm² at the stimulating electrode. Assuming even higher levels of stimulation, 25 mA at 250 μsec, the maximum charge density per phase is 0.79 μC/cm². At these levels, the charge density is generally 12 to 120 fold less at the stimulating electrode than the maximum allowed at the cerebral cortex. Since the cortex is a minimum of 10-13 mm from the stimulating electrodes, and given the interposed layers of skin, fat, bone, dura, and CSF, the actual charge densities will be significantly lower. This is of importance in avoiding the undesired passage of current directly through brain tissue as a bulk conductor.

As shown in FIG. 6, stimulation intensity responses in a subject with electrodes of surface area 7.92 cm², at pulse durations between 150-250 μsec, results in current densities at the scalp well below currently recommended current densities for transcranial stimulation, which are 25 mA/cm², and charge densities at the scalp significantly lower than safe charge densities at the cerebral cortex (0.15-0.18 μC/cm²).

Those skilled in the art will appreciate that various adaptations and modifications of the above described preferred embodiments may be configured without departing from the scope and spirit of this disclosure. Stimulation of the target nerve may be accomplished by cutaneous application of energy in many forms, such as magnetic or ultrasonic. Therefore, it is to be understood that the subject matter of this disclosure may be practiced other than as specifically described herein.

What is claimed is:

1. A system for trigeminal nerve stimulation for treatment of a neurological disorder or condition, the system comprising:
   a pulse generator; and
   a cutaneous electrode assembly in electrical communication with the pulse generator, the assembly comprising:
      a first electrode comprising at least one contact configured for cutaneous placement over an ophthalmic nerve on one side of a patient's forehead;

a second electrode comprising at least one contact configured for cutaneous placement over an ophthalmic nerve on an opposing side of the patient's forehead; and an insulating region surrounding each of the first and second electrodes.

2. A method for treating a neurological disorder or condition by trigeminal nerve stimulation, comprising:

aligning a cutaneous electrode assembly with the nasal midline of a patient, wherein the cutaneous electrode assembly includes a first contact separated from a second contact by an expected separation between the ophthalmic nerves on the patient's forehead;

applying the aligned cutaneous electrode assembly on the patient's forehead such that the first contact overlays a first one of the ophthalmic nerves and the second contact overlays a remaining second one of the ophthalmic nerves on the patient's forehead; and driving electrical signals through the applied cutaneous electrode assembly to treat the neurological disorder or condition.

\* \* \* \* \*